US009752967B2

(12) United States Patent
Pavels Petersen et al.

(10) Patent No.: US 9,752,967 B2
(45) Date of Patent: Sep. 5, 2017

(54) SAMPLE EXTRACTING, DILUTING AND DISCHARGING DEVICE

(71) Applicant: Bühlmann Laboratories AG, Schönenbuch (CH)

(72) Inventors: Erik Pavels Petersen, Porsgrunn (NO); Arne Roseth, Nesöya (NO); Thomas Jermann, Röschenz (CH); Jakob Weber, Pfeffingen (CH)

(73) Assignee: BÜHLMANN LABORATORIES AG (CH)

( * ) Notice: Subject to any disclaimer, the term of this patent is extended or adjusted under 35 U.S.C. 154(b) by 345 days.

(21) Appl. No.: 14/373,290

(22) PCT Filed: Jan. 18, 2013

(86) PCT No.: PCT/EP2013/050988
§ 371 (c)(1),
(2) Date: Jul. 18, 2014

(87) PCT Pub. No.: WO2013/107893
PCT Pub. Date: Jul. 25, 2013

(65) Prior Publication Data
US 2014/0352455 A1   Dec. 4, 2014

(30) Foreign Application Priority Data
Jan. 20, 2012   (EP) .................... 12151959

(51) Int. Cl.
*G01N 1/38* (2006.01)
*A61B 10/00* (2006.01)
*B01L 3/00* (2006.01)

(52) U.S. Cl.
CPC ............ *G01N 1/38* (2013.01); *A61B 10/0038* (2013.01); *B01L 3/502* (2013.01); *A61B 10/0096* (2013.01);
(Continued)

(58) Field of Classification Search
None
See application file for complete search history.

(56) References Cited

U.S. PATENT DOCUMENTS

| 7,048,693 B2 | 5/2006 | Zhou |
| 2006/0210448 A1 | 9/2006 | Wang |

(Continued)

FOREIGN PATENT DOCUMENTS

| DE | 102007057760 | 2/2009 |
| EP | 1366715 | 12/2003 |

(Continued)

OTHER PUBLICATIONS

WO2009136445, Makato et al., Machine English Translation Abstract, No Date.*

(Continued)

*Primary Examiner* — Jill Warden
*Assistant Examiner* — Julie Tavares
(74) *Attorney, Agent, or Firm* — Lerner, David, Littenberg, Krumholz & Mentlik, LLP

(57) ABSTRACT

A tube for extracting, diluting and discharging a sample: able to control the amount of discharged diluted solution in the tube, after the sample has been diluted; that improves the hygienic conditions of discharging the sample; that enables introduction of a predetermined amount of a sample in any liquid or solid state; and that is able to transfer a specific amount of a diluted sample into another tube for further processing without any hygienic problems and with no risk of accidents.

15 Claims, 9 Drawing Sheets

(52) U.S. Cl.
CPC ... *B01L 2200/0689* (2013.01); *B01L 2200/16* (2013.01); *B01L 2300/0609* (2013.01); *B01L 2300/0681* (2013.01); *B01L 2300/087* (2013.01); *B01L 2400/0644* (2013.01); *B01L 2400/0683* (2013.01); *G01N 2001/382* (2013.01); *G01N 2001/386* (2013.01)

(56) References Cited

U.S. PATENT DOCUMENTS

2008/0206852 A1   8/2008   Numajiri
2009/0005705 A1   1/2009   Wan

FOREIGN PATENT DOCUMENTS

| EP | 1371964 | 12/2003 |
|---|---|---|
| EP | 1384442 | 1/2004 |
| EP | 1986006 | 10/2008 |
| JP | 47016455 | 10/1972 |
| JP | 05256746 | 10/1993 |
| JP | 2001099763 | 4/2001 |
| JP | 2008203213 | 9/2008 |
| WO | 0051496 | 9/2000 |
| WO | 2006027054 | 3/2006 |
| WO | 2007070741 | 6/2007 |
| WO | 2009136445 | 11/2009 |

OTHER PUBLICATIONS

Translation of Japanese Office Action mailed Oct. 2, 2015 in Japanese Application No. 2014-552646.
International Search Report issued in PCT/EP2013/050988 mailed Jun. 18, 2013.
International Preliminary Report on Patentability and Written Opinion issued in PCT/EP2013/050988 issued Jul. 22, 2014.
Partial European Search Report completed Oct. 31, 2012 in European Application No. 12 15 1959.

* cited by examiner

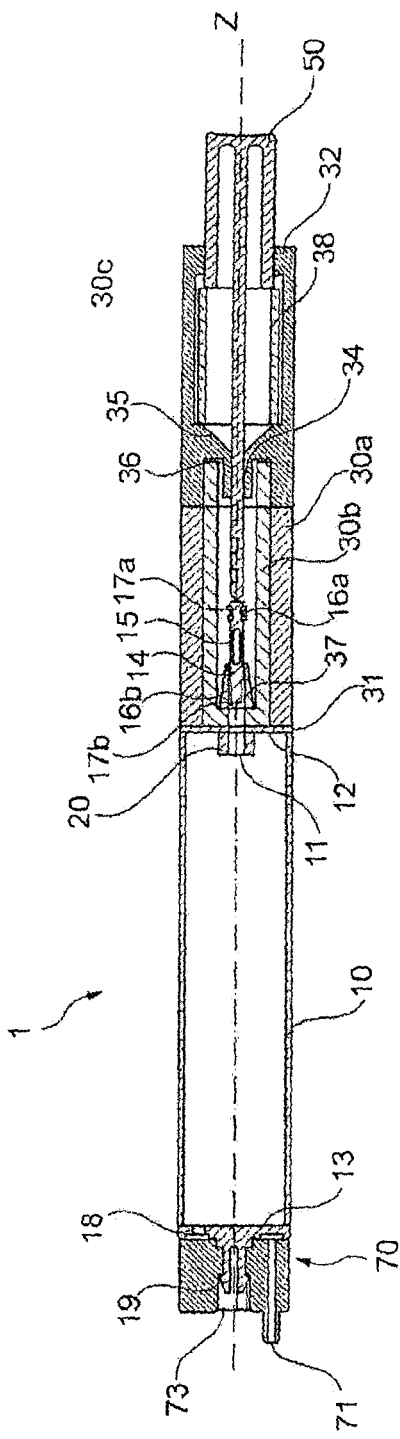
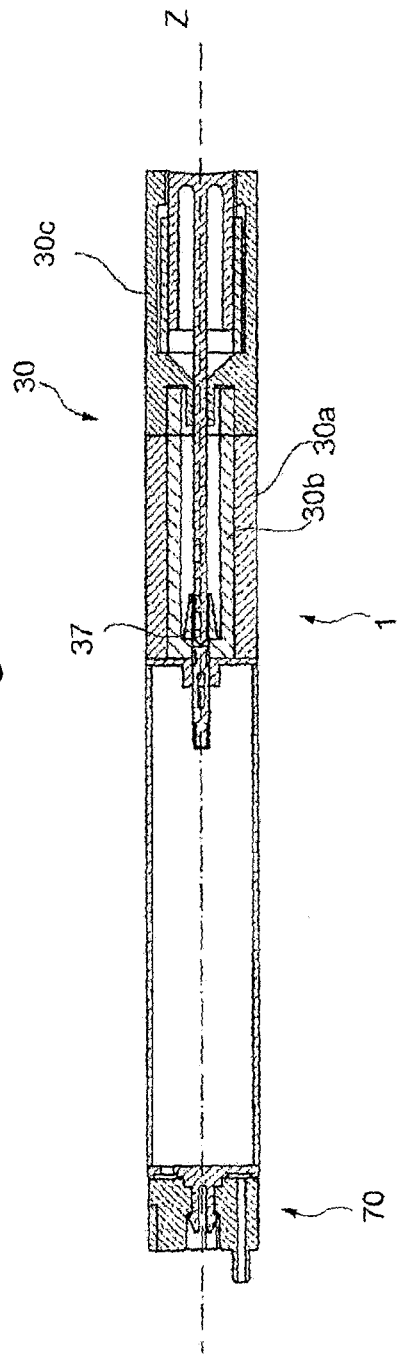
Fig. 1a
Fig. 1b

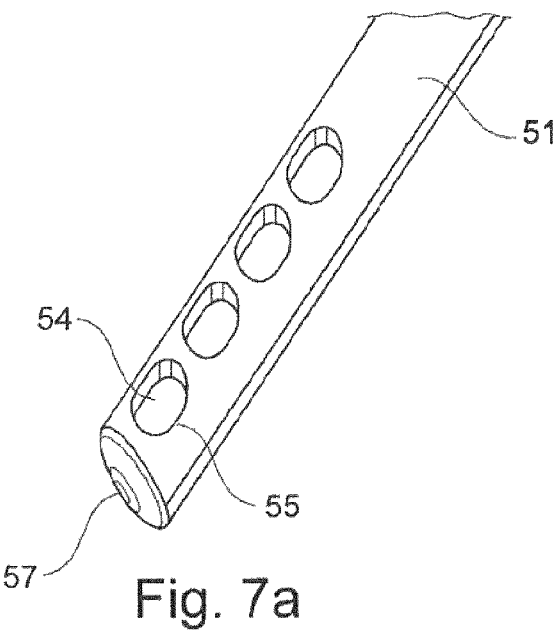
Fig. 7a
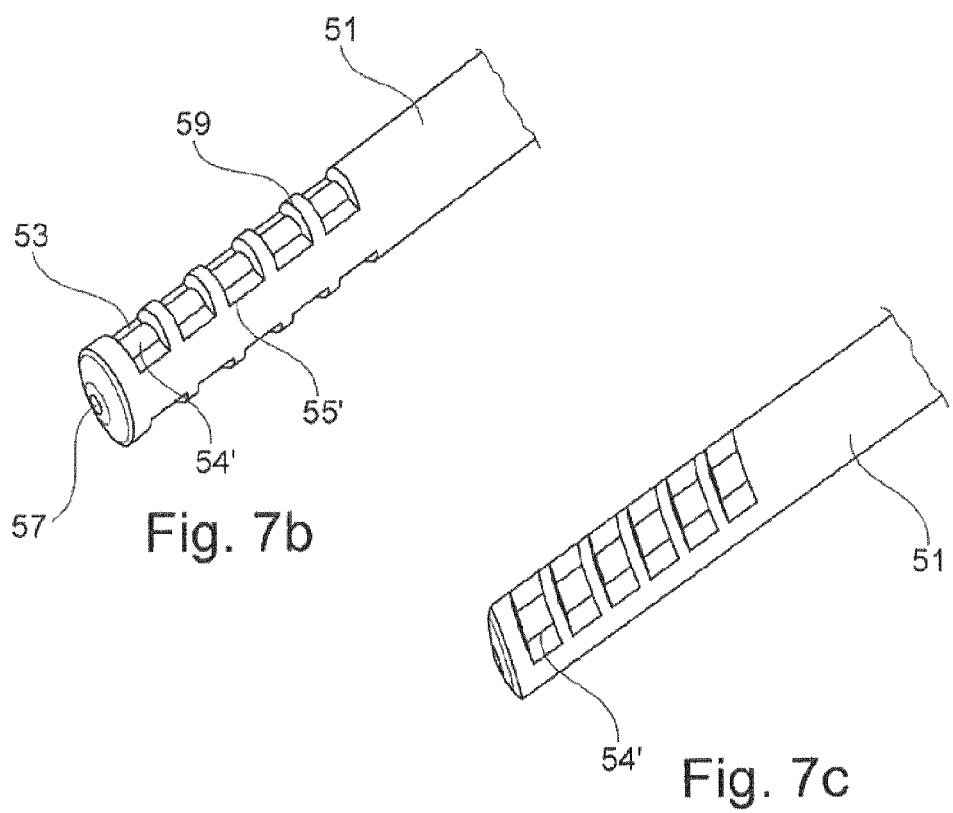
Fig. 7b
Fig. 7c

SAMPLE EXTRACTING, DILUTING AND DISCHARGING DEVICE

CROSS REFERENCE TO RELATED APPLICATIONS

This is the U.S. National Phase application of PCT International Application No. PCT/EP2013/050988, filed Jan. 18, 2013, and claims priority to European Patent Application No. 12151959.9, filed Jan. 20, 2012, the disclosures of each of these applications being incorporated herein by reference in their entireties for all purposes.

FIELD OF THE INVENTION

The invention refers to a stool extracting, diluting and discharging device and, in particular, to a sample transferring device. Furthermore, the invention refers to a method for collecting, diluting, mixing and discharging a stool sample.

BACKGROUND ART

Several devices and methods have been used in the past to collect, preserve, transport, dilute and discharge chemical, environmental or biomedical specimens, including in particular fecal samples for later analysis by a laboratory or for clinical studies. One problem with specimen contaminated with germs is in particular the hygienic component of collecting the samples and diluting them in an appropriate tube.

DE 10 2007 057 760 B3 discloses a device for collecting and dissolving a pastry sample. The sample pin of this device has a hollow end part for collecting the sample. The end part comprises further windows or openings in its side wall. When the sample in the sample pin is dissolved in a solution chamber, the end part of the chamber can be broken off and the dissolved sample can be discharged.

U.S. Pat. No. 7,048,693 B2, EP 1384442 B1 and US 2006/0210448 A1 show a specimen collection, storage and transport device with a sample pin for collecting the specimen. This sample pin has a handle and an elongated pin with a spiral-shaped end. This end is put into a sample to be probed, pulled out again and shoved into the corresponding tube. The tube is divided into two sections, an upper section and a lower section. The separation wall between these two sections comprises a hole through which the sample pin and in particular the spiral-shaped end is pushed and a certain amount of the collected sample can be brought into the second section. This second section is filled with a solution. By agitating the tube after the sample pin has been closed by screwing it into the tube via complementary threads, the sample is diluted in the solution.

To discharge such a diluted sample, for example to put a certain amount of the diluted sample on an analytical test strip or a test plate or any other device, the discharge port comprises a breakable closure, which is opened by breaking off the tip of the discharge port. After that, the diluted sample can be discharged through the broken tip by pressing the body of the tube.

One problem is that the samples are not always of the same structure. That is, the samples can vary from a very liquid state to a very solid state. Thus, with the above-mentioned prior art tubes, or more particular with the sample pins used therewith, it is difficult to take a predetermined amount of a sample which is either very solid or very liquid. For example, in a very liquid sample the spiral-shaped end of the sample pin is not ideal of keeping the sample on the sample pin, because a liquid sample will drop off the sample pin.

Therefore, it is very difficult to get a predetermined amount of such a sample into the tube. There are also other solutions, like a spoon-shaped device or circumferential recesses at an end of a sample pin, as can be seen in various other documents.

However, with the circumferential recess the same problems occur as with the above-mentioned spiral-shaped pin according to the state of the art, whereas a spoon-shaped device makes it very difficult to get a specific amount of a sample, because the sample will adhere at the bottom of the spoon and this bottom cannot be scraped off by a through-hole as can the sample pins of the above-mentioned prior art.

A further disadvantage of the prior art is that discharging of the diluted sample via the breakable closure is difficult to control. By or after opening the discharge port it may happen that pressure is brought onto the tube and some of the diluted sample is discharged by accident. Finally, once opened, the types of prior art tubes cannot be closed again and, thus, it is very difficult or impossible to store them and use again for a second test and the like.

Another problem occurs when the diluted sample should be transferred into another tube for further processing, i.e. mixing the already diluted sample with the same or another solution for further diluting (some medical utilizations need highly diluted samples and/or a dilution buffer different from the first buffer or liquid). For this purpose, a pipette is generally used to transfer a predetermined volume of the diluted sample contained in the tube. Thus, the tube has to be opened and the pipette has to be inserted into the tube. However, this is a possible source for contamination of the sample and also hygienically not free of risks. Therefore, the above mentioned devices are even not suitable for near patient testing. Moreover, if the sample has to be further processed, home testing by a patient is impossible with these tubes, because the danger of contaminating the test sample with foreign particles as well as contamination of the environment and the user himself with the test sample is simply too high by untrained persons using a pipette.

SUMMARY OF THE INVENTION

An object of the invention is therefore to provide a tube for extracting, diluting and discharging a sample, wherein the tube is able to control the amount of discharged diluted solution in the tube, after the sample has been diluted, and that improves the hygienic conditions of discharging the sample. Furthermore, the tube assembly should also enable introduction of a predetermined amount of a sample in any liquid or solid state. Furthermore, a further object of the invention is also to transfer a specific amount of a diluted sample into another tube for further processing without any hygienic problems and with no risk of accidents.

According to the invention, a tube for mixing, diluting and preserving a sample comprises a hollow first container for receiving and storing a solution, the first container having first and second ends, wherein at least the first end has a through-hole; and a transport-pin located in the through-hole of the first end having a shape closely matching to the through-hole, the transport-pin comprising a recess with a predetermined size, the recess is suitable to be filled with a sample, wherein the transport-pin is movable between an initial position in which the recess is positioned at least partially on the outer side of the first container, and an end position, in which the recess is positioned at least partially on the inner side of the first container. With this arrangement it is basically possible to collect a predetermined amount of a sample in the recess and to introduce it into the tube by pushing the transport-pin into the tube. Furthermore, this is the basic structure for a tube able to transport a predetermined amount of a diluted sample efficiently into another tube.

Furthermore, the transport-pin and/or through-hole comprise a latch that prohibits unforced movement of the transport-pin in its initial position and/or end position. In particular, in the end position the latch preferably locks the movement of the pin completely, i.e. also against a higher pushing force. This secures the tube against accidental leaking of the diluted sample or introduction of unwanted particles.

The transport-pin and/or the through-hole can also comprise at least one seal for sealing the through-hole when the transport-pin is in its initial position and/or the end position. The seal can also seal not only the initial and the end position, but can also cover all positions between them. In particular, the seal is disposed on the latch or the latches. The seal then can be formed such that it provides both effects securing the transport-pin against unwanted movement and sealingly closing the through-hole. This reduces the complexity of the constructions of the tube, since one single element can provide both functions.

The first end of the container is formed detachable, so as to open the first container at the first end. By this, it is firstly possible to increase the flexibility of the tube by changing the transport-pin according to its needed function (e.g. different predetermined volumes), and secondly, if necessary, the diluted sample can also be accessed from the outside with tools like a pipette.

The tube can further comprise a second container for receiving and storing a solution, the second container is located with one distal end on the first end of the first container such that the transport-pin protrudes into the second container, and the second container further comprises a proximal end and an opening suitable for inserting a sample pin. Such a construction enables the tube to dilute and mix a sample introduced by the sample pin into the second container and then transport a predetermined amount of the diluted sample into another solution for further diluting and mixing. In contrary to the state of the art, the transport-pin is then used as a very hygienic means for transferring a diluted sample from one tube to another. Thus, the transport-pin enables a clean, hygienic and secure transportation of a predetermined amount of a diluted sample to another tube (e.g. for further dilution and/or liquid exchange).

The proximal end of the second container is suitable to receive the sample pin such that the sample pin is moveable into a first position, in which the sample can be brought into contact with the solution contained in the second container, and to a second position, in which the sample pin pushes the transport-pin from the initial position into the end position. By forming the second tube in that way, it is secured that the transport-pin only transfers a sufficiently mixed and diluted sample of the second container into the first container. Moreover, the sample pin can also be used to move the transport-pin, which eases the construction of the transport-pin.

The opening of the second container is preferably formed with a transversal septum having an axial passageway therethrough. This transversal septum eases introducing a sample pin into the tube and it can be used to remove substance of the sample, which is in excess and/or not in the correct place (e.g. not in the recesses of the sample pin).

The proximal end of the second container can be formed suitable to accommodate the sample pin and further comprise a guide groove for guiding the movement of the sample pin. By accommodating and guiding the sample pin, the movement of the sample pin can effectively be controlled.

The sample pin is fixable in the first position and/or a second position such that the sample pin is logged from retraction. Thus, once inserted into the second tube, the sample pin can be used to seal the opening of the proximal end of the second container. Additionally, once pressed further inwards to move the transport-pin, the sample pin can also serve to avoid accidental backward movement of the transport-pin.

The sample pin can also be blocked from further movement in at least the inserting direction, when the transport-pin is in its end position. That secures, that the sample pin does not accidently push the transport-pin entirely into the first container, thereby accidently opening the passage between the first and the second container.

Furthermore, the tube can comprise a sediment portion or a filter to sediment or retain the debris of the sample after its homogenization or after mixing and diluting the sample. This is an effective way of separating sediment and diluted sample from each other, so that the transport-pin only transfers the diluted sample and not sediments. Thus, the final analytical results will be more precise.

According to the second aspect of the invention, a tube for mixing, diluting, preserving and discharging a sample comprises a hollow first container for receiving and storing a solution, the first container having first and second ends, wherein the first end has a first through-hole suitable for inserting a pin having a shape matching to the through-hole, the second end has a discharge port suitable for discharging a diluted sample, and a first fitting element; and a discharge device for controlling discharge of the diluted sample via the discharge port, the device having a discharge-opening for discharging the diluted sample and a second fitting element, that cooperates with the first fitting element to mount the discharge device on the first container, wherein the discharge device is movable between at least two positions, preferably between a discharge position and a closed position. Providing such a discharge device enables the tube to be properly closed before and after use and, thus, hygienically stored or used repeatedly. Preferably, the discharge-opening is connected with the discharge port in the open position. This construction enables a controlled and hygienic discharge of the diluted sample. Particularly, the first position is a closed position, in which the sample cannot be discharged, and the second position is a discharge position, in which the sample can be discharged.

The discharge device can comprise a volume like a chamber for receiving a predetermined amount of the sample solution. This volume allows a discharge of a predetermined amount of the diluted sample.

Furthermore, the discharge device can comprise a vent or a valve that preferably connects the volume to the outside of the tube. That enables for example the introduction of air, thereby easing the discharge of the liquid out of the volume.

The discharge device can further comprise gripping means for supporting the manual actuation of the movement of the discharge device. This makes the use of the discharge device easier.

The discharge device can further comprise a moveable plate that serves to control the discharge of the sample. Such a moveable plate is preferably rotated within the discharge device. In particular, the moveable plate comprises a predetermined volume that is in the first position connected to the discharge port of the first container and in the second position connected to the discharge-opening of the discharge device. In this manner, a defined amount of liquid can be securely discharged. The moveable plate can comprise a seal provided on at least one side for sealing the discharge device from leakage of the sample. This is particularly useful to enhance the hygiene of the tube.

The movement of the discharge device and in particular of the handle can be restricted by at least one stopper. Furthermore, the tube may comprise a cap for covering the discharge device and blocks movement of at least the moveable part of the discharge device. Thus, as long as the cap is in place, the tube and the discharge device is protected from being accidentally used, respectively.

The fitting elements can be formed as a protruding pin and a complementary recess, around which the discharge device is rotatable. A rotation movement between at least two positions, e.g. the closed and the discharge position, is a very hygienic way of moving the discharge device, since then all parts in contact with the discharge-opening of the first container are always covered without additional elements. Another possibility of a tight fixture is if the fixing portion is formed as welding rings on the circumference of the discharge device and the second end of the hollow first container.

The geometry of the discharge port and/or the discharge-opening can allow a quantitative and predetermined volume transfer of the liquidized and diluted sample. That is another possibility to discharge a predetermined amount without a very complicated structure. The geometry can therefore be formed such, that a drop of a predetermined volume of the liquidized and diluted sample will fall off, when it has achieved a predetermined size.

Furthermore, the second end of the first container can be formed detachable so as to open the first container at the second end. This enables the tube to be precisely adjusted onto the necessities, for example by fitting an appropriate discharge device on the second end. However, the interior of the first container can also be accessed by opening the second end.

The above-mentioned tubes can all be combined together. In particular, the first tube with the transport-pin and the tube with the discharge device have a synergistic effect, since the transport-pin increases the pressure in the tube, while the discharge port can control the discharged liquid by the pressure difference. Thus, a combination of both tubes can provide a better control of the discharge liquid. For example, such a combination contains a hollow first container, the transport-pin and a discharge device.

Another aspect of the invention relates to a tube for mixing, diluting, preserving and discharging a sample comprising a hollow first container comprising a solution and a device for discharging the solution and a hollow second container also comprising a solution and an introduction port for introducing a sample pin, wherein the first container and the second container are connected by a transfer device that enables at least a sealed transfer of the solution in the second container into the first container. Such a tube provides a safe and hygienic transfer of the solution of one tube to the other. Thus, such a tube is highly practical for home use by a patient, in particular if the diluted sample has to be further processed. This tube can comprise one or more of the above mentioned features, in particular the features of claims 1 to 12 and/or claims 13 to 19. In particular, the first and second container can be fixed together, preferably at their ends opposite to the discharge device (which can also be basically a breakable discharge device of the prior art). The transfer device can be a transfer pin as described in this invention, but can also be for example a (preferably manually driven) sleeve pump or hose pump combined with one or two one-way-valves disposed at the pump device. The valve (s) enable (s) the solution to flow from the second container to the first container, but restricts flowing in the opposite direction. Another embodiment of such a transfer device is a third tube that is disposed between the second and the first containers and being adapted to be opened and closed to the second container for being filled with the solution and stopping the flow connection and being adapted to be opened and closed to the first container, to further dilute the sample of the second container therein. However, a direct flow-connection between the second and the first container should be avoided. Thus, the third container should not be opened to the first and second containers simultaneously.

According to the invention, a sample pin for collecting a sample comprises an elongated pin including a handle located at a proximal end of the elongated pin and at least one recess with a predetermined volume preferably located at a distal portion of the elongated pin, wherein the recess comprises only one opening with one edge, wherein the complete edge of the opening is above the bottom of the recess when seen in a side-view and the opening is facing upwards. This recess with its spoon-like shape enables collection of a sample in any condition, in particular of a very liquid sample. The liquid cannot flow away or drop off this recess. However, for any sample comprising a normal consistency a sample pin comprising a different shaping and arrangement of the recesses, such as described in the state of the art, can be used interchangeably without loss of proper functionality.

In particular, there is provided a plurality of recesses and the openings of the recesses are preferably facing all in the same direction.

The distal tip of the pin can comprise a tapered portion. This tapered portion can be cone-shaped or round, and eases introducing the sample pin into a very solid sample as well as into the tube.

Preferably, the handle of the sample pin can comprise a protrusion that protrudes outwards from the circumference of the handle. This protrusion can be used for guiding the sample pin and for blocking its movement in either direction. The above sample pin can be used with any of the above-mentioned tubes, in particular with a combination of the above-mentioned tubes.

Another sample pin for collecting a sample according to another aspect of the invention comprises an elongated pin including a handle located at a proximal end of the elongated pin and at least one recess with a predetermined volume preferably located at a distal portion of the elongated pin, wherein the recess has the shape of a circumferential groove, that has an circumferential angle of maximum 180 degrees. The circumferential angle can be measured along the edge, with respect to the center of the elongated pin and/or with respect to the inside surfaces of the side edges of the recess. In such a sample pin, a more liquid sample can be better kept in the recess. The circumferential angle is measured from the center of the preferably cylindrical elongated pin or from the middle of the bottom plane with respect to the top of the cutout sides of the recess. Additionally, the shape of the recess is highly practical for flushing out the sample contained in the recess. Furthermore, there can be two or more recesses and they can be provided on opposite sides or pointing in different directions of the elongated pin. However, preferably two or more of these recesses are facing in the same directions. In another embodiment, the bottom of the recess is flat or has a deepened shape.

According to the invention, a method for collecting, mixing diluting and discharging a sample comprises the steps of collecting a predetermined amount of a sample with a sample pin, introducing the sample pin containing the sample into a second container filled with the extraction and/or dilution solution and containing a transport-pin comprising a recess, mixing the sample with the solution contained in the second container, moving a predetermined volume of the mixed sample from the second container to the first container by pushing the transport-pin with the recess filled with the mixed sample into the first container. This method enables a clean and easy way to further dilute a diluted sample, thereby ensuring that the final dilution of the diluted sample is predetermined by the fixed volume of the recess and the predetermined amount of solution in the first and/or second container.

By introducing the sample pin into the second container, excess sample on the sample pin can be stripped off by a transversal septum. That ensures firstly a smooth introduction of the sample pin into the tube and, secondly, that only sample present in the recess (es) of a sample pin are introduced into the tube.

Furthermore, the method can comprise the step of separating the debris from the mixed sample by sedimenting or filtering the mixed sample, wherein this step is carried out prior to moving the transport-pin into the first container. These features enable that the transport-pin only transfers the diluted sample and not solid particles into the first container.

The method can further comprise the step of opening a discharge port of the first container and quantitatively discharging the diluted sample to a discharge-opening. Furthermore, the diluted sample is automatically and quantitatively discharged out of the first container by gravitational force supported by a vent, by a pressure difference and/or by compressing the first container. This allows a pipetting-free transfer of the liquidized and diluted sample and a good control of the discharge amounts of the sample solution.

The method can also comprise the step, that the mixed sample is loaded into and discharged from a volume to a discharge-opening.

Finally, the discharge volume can be further controlled by the geometry of the discharge port and/or the discharge-opening.

These above-mentioned methods can be combined with any of the above-mentioned tubes and/or a sample pin.

Another aspect of the invention is a tube for mixing, diluting, preserving and discharging a sample, comprising a hollow first container for receiving and/or storing a solution, the first container having first and second ends, wherein the first end has a first through-hole suitable for inserting a sample pin having a shape matching to the through-hole, the second end has a discharge port suitable for discharging a diluted sample, wherein the hollow first container has a guide disposed on the first end of the first hollow container which interacts with the sample pin to guide the sample pin in a predetermined position. Such a guide eases handling of the sample pin, in particular after the collection of a sample and can support the opening action for the user. The guide has preferably inclined portions.

The guide comprises a receiving slot in a predetermined position for receiving the protrusion of the sample pin in the final position. The final position is in particular the second position and improves the control of movement of the sample pin.

The tube can further comprise a sample pin for collecting a sample, the sample pin comprises an elongated pin, a handle located at a proximal end of the elongated pin, and at least one recess with a predetermined volume formed in a distal portion of the elongated pin, wherein the handle further comprises a protrusion that interacts with the corresponding guide. The protrusion can comprise a tapered or inclined end in insertion direction. This improves the guidance by the guide. However, the protrusion can also have a round shape.

A further aspect of the invention is a tube for mixing, diluting, preserving and discharging a sample, the tube comprises a hollow first container for receiving and/or storing a solution, the first container having first and second ends, wherein the first end has a first through-hole suitable for inserting a sample pin having a shape matching to the through-hole, the second end has a discharge port suitable for discharging a diluted sample, wherein the hollow first container comprises locking means for locking a sample pin in a first position located at the first end of the hollow first container. This ensures a safe delivery of a properly closed tube.

The tube may further comprise second locking means for locking the sample pin in a second position located further in insertion direction than the first position. The second locking means preferably prevent retraction of the sample pin. In addition to a safe delivery and due to the hygienically aspect, after use the second locking means prohibits that the tube is opened by accident or normal handling.

The first locking means can comprise a rib or a groove disposed on a circumferential portion of the first end of the first container, preferably not on the complete circumference (although it is possible).

Also the second locking means can comprise a rib or a groove disposed on the circumference of the accommodating part, preferably around the complete circumference.

Such a tube can further comprise a sample pin having an elongated pin, a handle located at a proximal end of the elongated pin, and at least one recess with a predetermined volume formed in a distal portion of the elongated pin, wherein the handle comprises at least one locking portion corresponding to the first and/or second locking means.

The sample pin can further have a gripping portion, particularly formed as pressing portion that serves to deform the handle to unlock the sample pin from the first position. This is a convenient but also secure way to firstly open the tube.

Finally, a tube may comprise the guide and/or the locking means and/or a discharge device as depicted above.

BRIEF DESCRIPTION OF THE FIGURES

FIG. 1a shows a longitudinal section of a tube comprising a transport-pin, a discharge device, a first and a second container and a sample pin, wherein the transport-pin is in a first or initial position;

FIG. 1b shows the tube of FIG. 1a, wherein the transport-pin is in the second or end position in the first container;

FIGS. 2a-g show isometric views of exemplary single parts of the embodiment of FIG. 1a;

FIGS. 7a-c show embodiments of the recesses according different aspects of the invention;

PREFERRED EMBODIMENTS OF THE INVENTION

Figure 2:
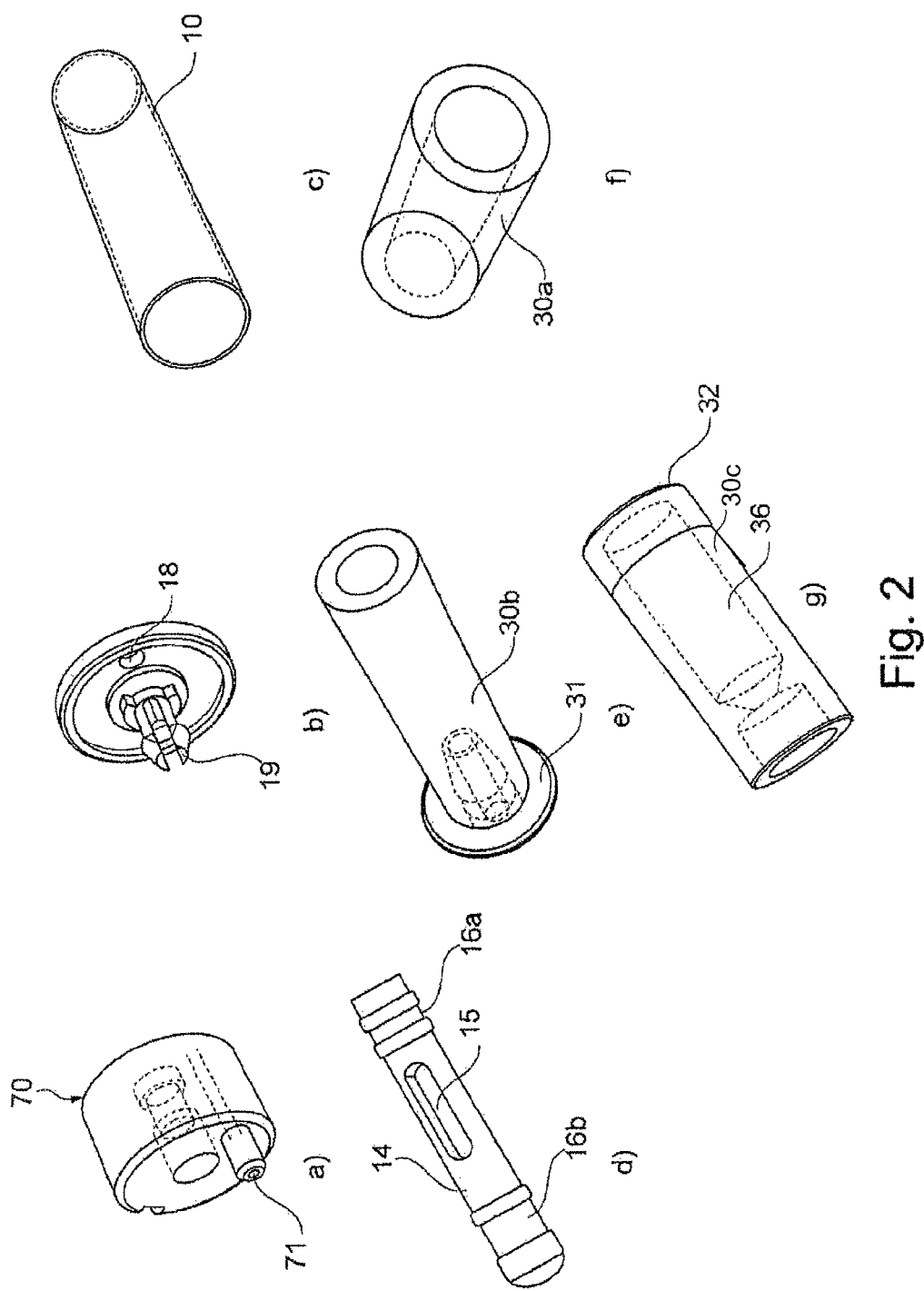
Figure 3:
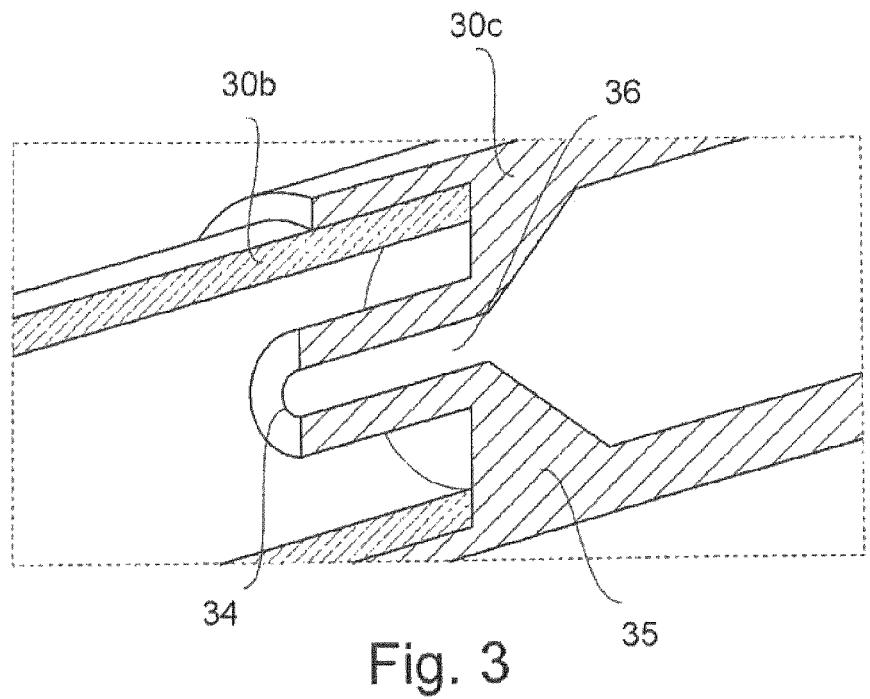
FIG. 3 shows an enlarged view of a part of the second container, in which the cap is fitted to the liquid containing part.

Referring now to FIGS. 1a and 1b, an embodiment of the invention is described in the following. Possible optional embodiments will be described as alternatives when the respective element is explained in the description.

The embodiment in FIG. 1 comprises a first hollow container 10 that is capable of receiving and storing a solution in which a collected sample can be mixed, liquidized and/or homogenized. The first container has a first end 12 and a second end 13, which can both be closed by an end-wall integrally formed on the hollow container 10, or which can be formed by an openable wall, for example a wall that is screwed onto or into the first container 10, or fixed on the container like a plug by shape-fitting.

In the first end 12, the hollow first container 10 comprises a trough-hole 11. In this through-hole 11 is located a transport-pin 14 that has preferably a shape that closely matches the shape of the through-hole 11. The transport-pin 14 comprises a recess 15 with a predetermined size. This recess 15 can be filled with a sample or a sample that is already diluted with a solution. The recess 15 can comprise a bottom wall and side walls, but can also be formed as a through-hole in the transport-pin 14. The transport-pin 14 can furthermore comprise a plurality of such recesses. In FIG. 1a, the entire recess is outside of the first container 10. However, it is sufficient, if the recess 15 is only in part on the outer side of container 10, as long as the recess does not provide a connection between the inner side of the first container 10 and the outer side of the first container 10. I.e. as long as the recess 15 is at least in part on the outside of the container, no particles, no sample or anything else can infiltrate the container through the through-hole 11. In the preferred embodiment shown in FIG. 1a, the recess 15 is formed as a through-hole.

The transport-pin 14 is moveable between an initial position (as show in FIG. 1a), which is the position with the recess at least partly outside the first container 10, and an end position (as shown in FIG. 1b), in which the recess 15 is positioned at least partially on the inner side of the first container 10.

The transport-pin 14 can be press-fitted into the through-hole 11. However, it is preferred that the transport-pin 14 and/or through-hole 11 comprises at least one seal 17a, 17b for sealing the through-hole 11 when the transport-pin 14 is in its initial position and/or the end-position. The seal 17a, 17b can be disposed at the through-hole 11 and can be made of rubber, silicon, Teflon, ceramic, any kind of plastic or synthetic material or any other suitable material. The seal 17a, 17b can also be disposed at the transport-pin 14. In the example shown in the FIGS. 1a and 1b, the seal 17a is located at a position that will be in contact with the through-hole 11 in the end position 3 of the transport-pin 14, and the seal 17b is in a position which will be in contact with the through-hole 11, when the transport-pin 14 is in its initial position. However, the whole transport-pin 14 can be covered by a seal 17a, 17b as long as the recess 15 is not covered as well. Also, the transport-pin 14 and the through-hole 11 can comprise both a seal. The seal 17a, 17b at the through-hole 11 and the seal at the transport-pin 14 may then be of different materials, so as to provide an easy movement of the transport-pin 14 within the through-hole 11. However, the material of the seal 17a, 17b at the transport-pin 14 in the region of the initial position and the end position can also be made of a different material than the rest of the seal on the transport-pin 14, e.g. with a very high friction in view of the through-hole 11, to stop the transport-pin 14 if it is in the initial position or the end position.

Furthermore, the transport-pin 14 and/or the through-hole 11 can comprise at least one latch 16a, 16b that prohibits unforced movement of the transport-pin 14 in its initial position and/or the end position. The latch 16a, 16b can be formed into or onto the sealing 17a, 17b. The latch 16a, 16b is for example a protrusion in a radial direction of the tube 10 (in FIGS. 1a and 1b in a direction perpendicular to the center axis Z). The transport-pin 14 and/or the through-hole 11 can then comprise a corresponding recess, with which the protrusion will engage and latch. The latch can be made of any kind of silicon, Teflon, ceramic, any kind of plastic or synthetic material or any other suitable material, but preferably of a rubber or rubber-like material, to provide suitable sealing functions.

In the embodiment shown in FIGS. 1a and 1b, the through-hole 11 is formed as a longitudinal cylinder-shaped hole, which is formed into an extension 20 that extends along the center axis Z in an axial direction. However, the hole can be formed in any kind of geometry.

The transport-pin 14 can be guided in the through-hole 11 by guiding grooves and corresponding guiding protrusions on the transport-pin. These grooves and protrusions (not shown in the Figures) could be formed in an axial direction in the through-hole 11 and in the transport-pin 14. However, it does not make any difference if the grooves are formed in the through-hole 11 or the transport-pin 14. Basically, these features are enough to make the tube working for mixing, diluting and preserving a sample. The recess 15 in the transport-pin can be filled with a sample and the transport-pin 14 can then be pushed by, for example, a cap (not shown) with a bigger diameter than the hollow first container 10, into the first container 10. After that, the sample can be mixed and diluted in the solution and stored in the hollow first container 10. This embodiment would then serve as a tube with an integrated sample pin.

However, the preferred embodiment as shown in FIGS. 1a and 1b includes a second container 30 for receiving and storing a solution. A solution can mean any liquid. However, it is possible to store a lyophilisate, a powder or other solid particles in one or both containers. To liquidize these particles, liquid like water has to be filled in the container storing the particles, before the sample will be diluted. This can be done for example by an extra valve, or, in case of the second container, through the opening for the sample pin. These liquidized particles are also meant by the term solution. In one embodiment, the second container 30 comprises an outer tube 30a (FIG. 2f), an inner tube 30b (FIG. 2e) and a proximal tube or cap 30c (FIG. 2g). These elements can be single parts, but they can also be formed integrally (in one piece). In the example shown in FIG. 1a, the first end of the container 10 is formed as a part of the inner tube 30*b*, as is the through-hole 11. However, the single elements of the assembly as shown in FIGS. 2*a* to 2*g*, are just one particular possibility to construct the tube 1, and the different parts of the tube 1 can be formed integrally, can be divided into additional single parts or can be divided into different parts than shown in FIGS. 2*a* to 2*g*.

The second container 30 is located with the distal end 31 on the first end 12 of the first container 10, such that the transport-pin 14 protrudes into the second container 30, and the second container 30 further comprises a proximal end 32 and an opening 34 suitable for inserting a sample pin 50.

The proximal end 32 of the second container 30, in this case the proximal tube or cap 30*c*, comprises an accommodating part 38 that is suitable to receive a sample pin 50. This accommodating part 38 can be formed in a way to interact with a sample pin 50, which will be described later.

In the second container 30, in particular in the inner tube 30*b*, is formed a sediment portion 37, which is preferably formed tapered or in a conical shape. Between the wall of the tube 30*b* and this sediment portion 37, debris and particles of the sample can settle down after its homogenization. In other embodiments, the sediment portion 37 can be replaced by a filter (not shown) such as a mesh or a fine net. Also fabric or other suitable tissue can be used as a filter that covers at least the recess of the transport-pin 14, but preferably the whole transport-pin 14 in the second container 30.

The opening 34 of the second container 30 can be formed as a transversal septum 35 having an axial passageway 36 therethrough. Such a transversal septum 35 eases introducing a sample pin 50 into the second container 30 and comprises additional features such as stripping off excess sample material present on such a sample pin.

Figure 4:
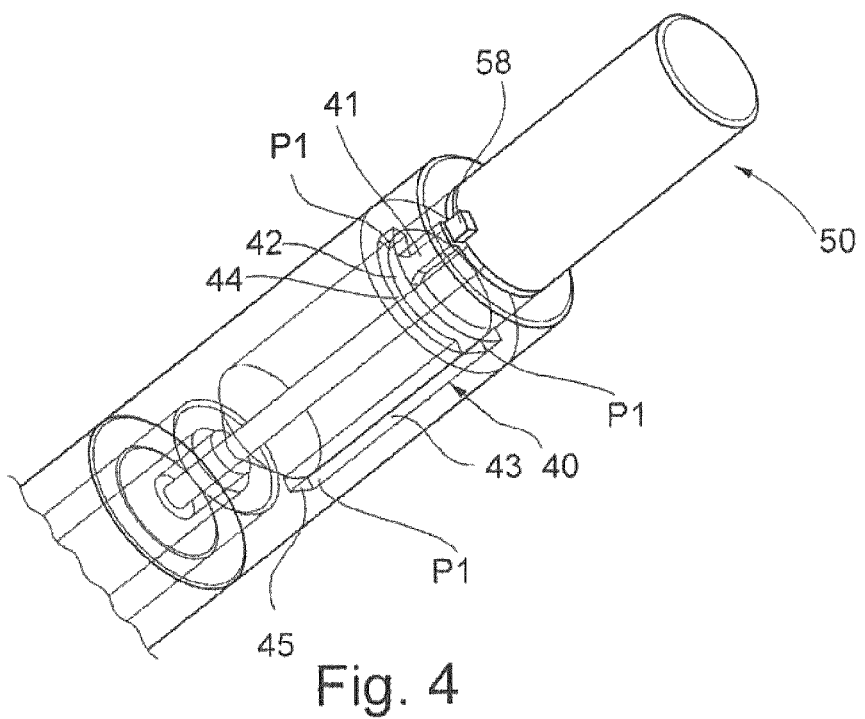
FIG. 4 shows an enlarged view of the cap including a guide groove and a sample pin including a protrusion.

The accommodating part 38 of the proximal tube 30*c* is formed such, that a sample pin 50 is movable into a first position (see FIG. 1*a*), in which the sample can be brought into contact with the solution contained in the second container 30, and to a second position, in which the sample pin 50 pushes the transport-pin 14 from the initial position into its end position (see FIG. 1*b*). The first position of the sample pin can thereby be indicated by, for example, a first rib which protrudes radially inwards in the accommodating part 38 of the proximal tube 30*c* (or single radial protrusions), and which are breakable to allow the sample pin to move further axially inwards in the second container 30. However, another possibility is to provide in the accommodating part 38 a guide groove 40 for guiding a movement of a sample pin 50. The guide groove 40 then can control the movement along the axis Z by interacting with a protrusion 58 of the sample pin 50. In the preferred embodiment, the guide groove 40 is formed by axially and circumferentially extending grooves 41, 42, 43. These grooves are shown in FIG. 4. The accommodating part 38 of the proximal tube or cap 30*c* can also be formed such, that a sample pin 50 is fixable in the first position and/or a second position such that the sample pin 50 is locked from rejection and/or further forward movement. In the preferred embodiment, this is carried out by the wall 44 of the circumferential guide groove 42 that blocks the protrusion from further axial movement in inserting direction. Additionally, the sample pin can be rotated into a blocked position PI (FIG. 4) after pushing it into the first position. By rotating the sample pin 50, the protrusion is moved in the guide groove 42 away from the axial extension 41 of the groove 40 (in FIG. 4 clockwise when seen from a top view), so that the sample pin 50 cannot be pulled back because the protrusion is locked axially in position PI. However, such a fixable first position could also be carried out by protrusions protruding radially inward in the accommodation chamber, and interacting with corresponding recesses or protrusions of the sample pin 50 like a clip. By providing these protrusions around the complete circumference of the sample pin, moving the sample pin 50 backwards can be made impossible.

In the preferred embodiment, the sample pin 50 is the rotated such that the protrusion moves from position P1 along groove 42 in the opposite direction (in FIG. 4 counter-clockwise) into position P2. Then the sample pin can be pushed into the second position until the protrusion 58 reaches position P3. A further axial movement in insertion direction is the blocked by the end wall 45 of groove 43.

The sample pin 50 can be blocked in the second position (FIG. 1*b*) from further movement in at least the inserting direction, when the transport-pin 14 is in the end position. This can be done either as mentioned above by the guide groove interacting with a protrusion 58 of the sample pin 50, or by protrusions protruding inwardly radially in the accommodating part 38. Also possible is a simple stopper in the accommodating part 38 and/or the end 32 of the accommodating part 38.

However, it is possible to form this accommodating part 38 on or in the proximal end of a first hollow container, as long as it is not wished to implement a transport pin. I.e. if a tube contains only one hollow container for mixing and diluting a sample, all features of the accommodating part 38 can be applied to such a tube, since the accommodation part serves for accommodation the sample pin which is necessary if the transport pin is not included in an embodiment. In this case the first and second positions can furthermore still be applied. With regard to FIG. 10, the accommodation part 38 is disposed on a first hollow container 10, which does not comprise a transport pin. The accommodation part 38 includes a first locking means 81, which is here formed as a groove 81 that interacts with a corresponding protrusion on a sample pin, which will be described later. This groove is preferably formed only on a circumferential portion of the accommodation part 38. A second locking means is provided further downstream relative to the inserting direction of the sample pin 50. This second locking means 82 can also be formed as a groove that interacts possibly also with the same corresponding element on the sample pin as the first locking means 81. The second locking groove is formed preferably around the complete circumference of the accommodation part 38. In this manner, the second locking means can prevent any further movement in axial direction of the sample pin once it is locked in the second locking means 82. Of course, the groove can also be a protrusion like a rib and interacts with a corresponding groove on a sample pin.

Figure 10:
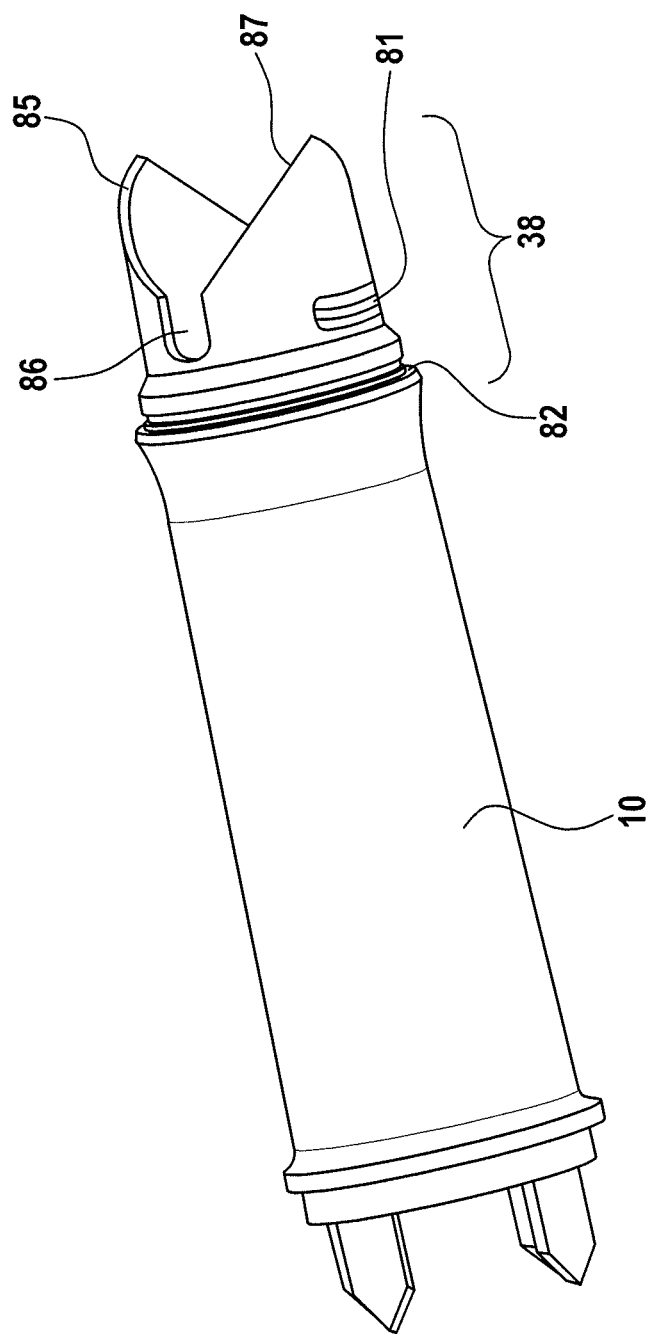
FIG. 10 shows a hollow first container according to the invention.

As already described above, the accommodation part 38 can also comprise a guide 85. In FIG. 10, this guide 85 is formed as a guide rail 87 which is preferably inclined and serves to guide a corresponding protrusion of a sample pin into a receiving slot 86. The interaction between a sample pin and the accommodation part with the first and second locking means 81, 82 and/or the guide 85 is described later. An accommodation part 38 can accommodate the handle of the sample pin within the accommodation part, but can also be inserted in the handle of the sample pin. In any case, it accommodates the elongated pin 51.

The first container 10 has at its second end 13 a discharge port 18 where it is suitable for discharging a diluted sample. On the second end 13 is furthermore provided a first fitting element 19. On the first container 10 is disposed a discharge device 70 for controlling discharge of the diluted sample via the discharge port 18. The device 70 has a discharge-opening 71, for discharging the diluted sample, and has a second fitting element 73, that cooperates with the first fitting element 19 to mount the discharge device 70 on the first container 10. At least a portion of the discharge device 70 is movable between two or more positions. These positions are preferably a discharge position, in which a diluted sample can be discharged, and a closed position in which the sample cannot be discharged. In one embodiment, the discharge device can sealingly cover the discharge port 18 in the closed position; and in the discharge position the discharge-opening 71 is then moved to a position where the discharge-opening 71 is connected with the discharge port 18, but closed towards to the first container 10.

Figure 5:
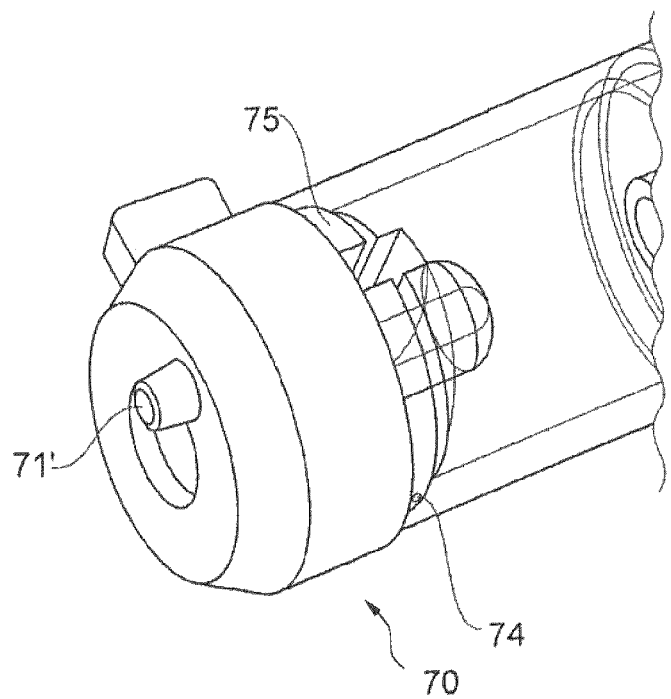
FIG. 5 shows a discharge device according to an embodiment of the present invention.
Figure 6:
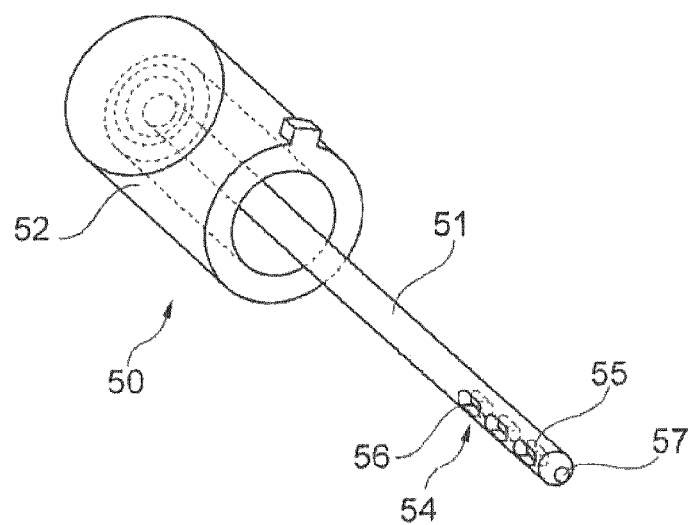
FIG. 6 shows a sample pin according to one embodiment of the present invention.
Figure 8A:
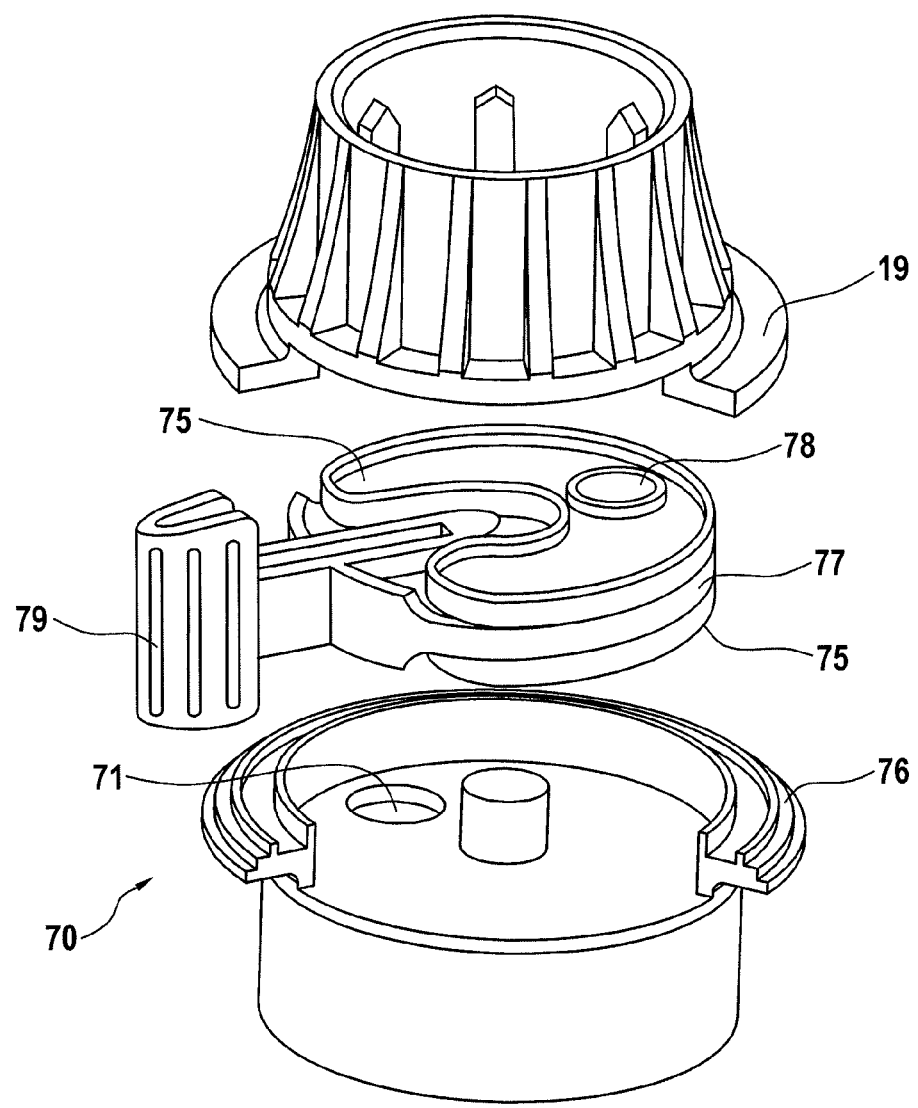
FIGS. 8a, 8b show a discharge device in an exploded view, including the second end of the hollow first container.
Figure 8B:
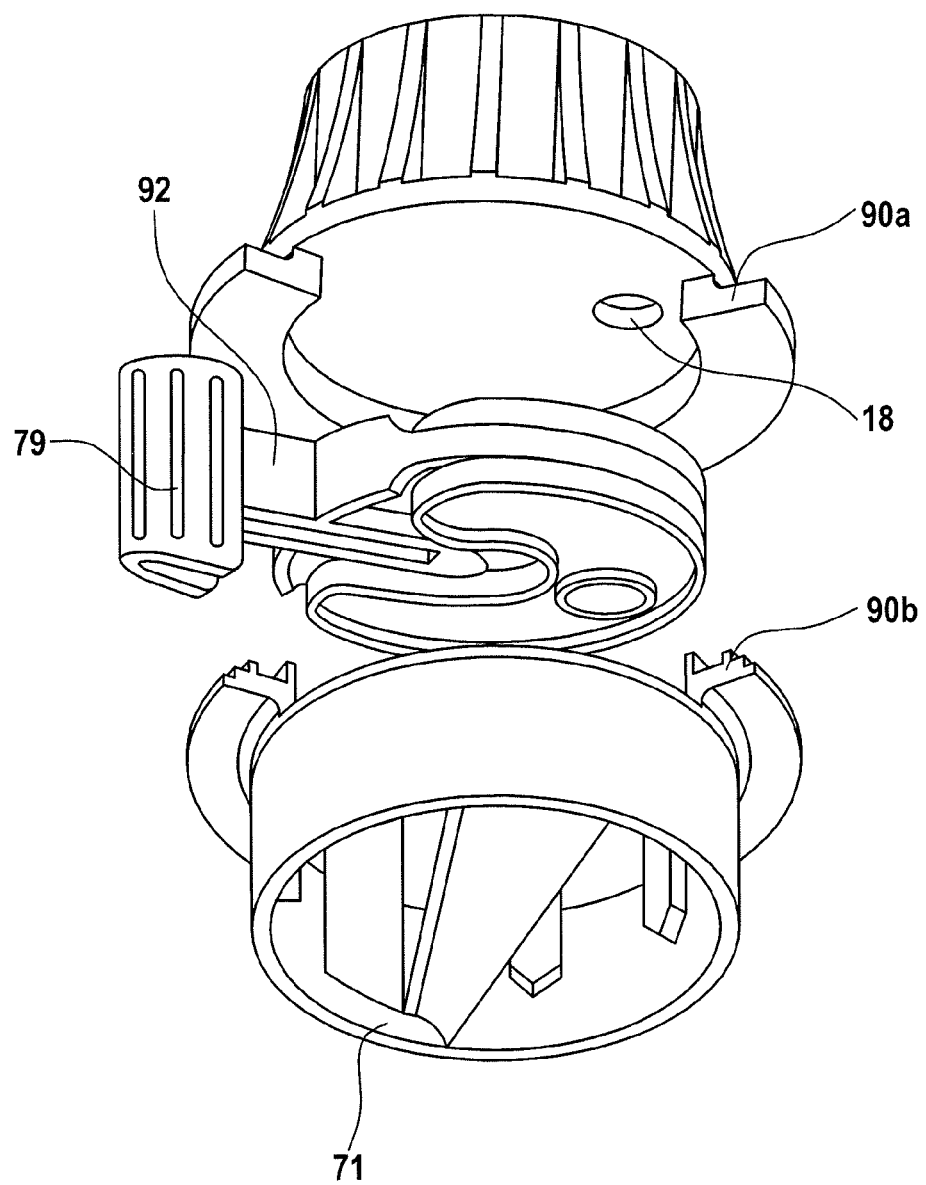

In another embodiment a volume like a chamber or a small container is provided. This chamber or small container has a predetermined volume 78 and is preferably located in the discharge device 70. In this embodiment, the discharge-opening 71' is relatively not moveable to the discharge port 18 of the hollow first container 10. Such a device is shown in FIGS. 5, 8a and 8b. It is preferred that in the closed position the volume 78, e.g. the chamber or small container, is connected to the discharge port 18 and is filled with a solution. In this case the discharge port 18 is big enough to not affect the mixing of the sample in the solution, i.e. that a total exchange of solution between the volume and the container 10 is secured. In this way it is also ensured that the volume 78 is filled with a properly diluted sample. Then the moveable portion 77 of the discharge device 70 is moved to the discharge position and the diluted sample is discharged out of the discharge opening 71'. However, the volume can also be initially in the discharge position, although it cannot initially contain sample liquid to be discharged. The moveable portion 77 of discharge device has first to be moved into the closed position to fill the volume 78 with a diluted sample. The volumetric discharge can be done as explained below, for example by a pressure in the hollow first container 10, by a pressure applied to the container 10 or by gravitational force preferably supported by a vent or valve (not shown) disposed somewhere at the first end 12 of the first container 10.

Additionally, the discharge device can also be moveable between three positions, an initial (closed) position, in which the volume is neither connected to the discharge port 18, nor to the discharge-opening 71', a second position, in which the volume is connected to the second container 10 via the discharge port 18 and is filled with the diluted sample, and an end (discharge) position, in which the sample can be discharged via the discharge-opening 71'.

The connection between the discharge device 70 and the hollow container 10 can be realized by fixing the discharging device 70 with a recess 73 complementary to the protruding pin 19. In FIGS. 1a and 1b, the protruding pin 19 is formed with a gap in the middle, to enable the functionality of a clip and engage with step-like portions in the corresponding recess 73. Around this protruding pin 19 the discharge device 70 can be rotated between at least two positions.

Furthermore the discharge device 70 can also be fixed on the hollow first container 10 by a welding portion 76. Such a welding portion can for example be disposed on a part of the discharge device 70 that does not need to be relatively moveable in view of the first hollow container 10. Then, a corresponding welding portion can be provided on the container as the fixing portion 19 and welded onto the welding portion 76 of the discharge device 70. In FIGS. 8a and 8b this welding portion 76 is shown as a circumferential ring that protrudes outwardly. In this manner, it is easy to access for welding.

Furthermore, the moveable portion 77 can be formed as a plate or cylinder including the above mentioned volume 78. A seal 75 can be provided on one or both sides of the moveable portion 77, e.g. a flat sheet made of rubber or silicone or any other suitable sealing material. The moveable portion 77 can comprise ribs on the outer surface to enhance the manual movement of the moveable portion 77. To further improve the handling of the moveable portion 77, a protruding handle 79 or grip can be provided. Furthermore, the movement of the moveable portion 77 can be restricted by stopping means 90a, 90b on the fixed part of the discharge device 70 and/or on the first hollow container 10, in particular at the second end 13 thereof. These stopping means 90a, 90b interact with corresponding abutment portions 92 on the moveable portion 77. In FIGS. 8a and 8b this is carried out by the circumferential welding portion 76 and the protruding handle 79. In both movement directions the handle 79 abuts with the abutment portions 92 against the stopping means 90a, 90b of the welding portion 76 and is stopped from moving further. To protect the discharge device and the tube, a cap (not shown) can be provided. This cap covers the discharge device. The cap also prevents movement of the discharge device, either by sufficiently covering the moveable portion 77 (in particular completely), or by blocking the handle 79. Blocking the handle 52 can for example be carried out by a protrusion that protrudes upwards from the cap into the movement path of the handle 79. Such a protrusion can either have a simple recess in which the handle is locked as long as the cap is on the tube, or can be combined with the stopper 90a, 90b if they are formed on the tube.

Another possibility (not shown in the figures) is to design the second end 13 with rails in which the discharge device 70 can slide. Then, the discharge device could be pushed, for example with a thumb of the user, from the closed position to an open position, in which the discharge port 18 is connected with the discharge-opening 71. In this way, it is possible to ensure that on the one hand discharging the diluted solution is not possible by accident, and, on the other hand, the discharge-opening 71 can be closed again. However, to further avoid accidental opening of the discharge device 70, the discharge device can be connected with breakable connections with the second end 13 of the container 10 when it is in the initial, closed position.

The discharge device 70 can include a sealing 75, preferably in form of a ring made of rubber, silicon, Teflon, ceramic, any kind of plastic or synthetic material or any other suitable material. This sealing 75 is disposed between the moveable portion of the discharge device 70 and the static part, which is either the second end 13 of the first container 10 or a static part of the discharge device 70 fixed at the second end 13 of the first container 10. The sealing 75 seals the cut between the moveable portion of the discharge device and the static part so that leaking of the diluted sample can be avoided, in particular with regard of a movement of the moveable portion of the discharge device 70.

The volumetric discharge of the diluted solution can be carried out by pressure, which is increased in the hollow first container 10, for example due to the transport-pin 14 pushed into the first container 10. Another possibility is to define the geometry of the discharge port 18 and/or the discharge-opening 71 to allow a quantitative and predetermined volume transfer of the liquidized and diluted sample. That is, the opening has a size to enable that a drop with a predetermined size will drop off the opening. In particular, the liquid will be slowly come out of the discharge device 70 until the opening cannot hold the increasing drop at the discharge-opening 71 of the discharge device 70. The force to get the liquid out can be simple gravitational force supported by a vent or valve 74, can be the pressure inside the first hollow container 10 or can also be a pressure applied on the container, for which the container itself should be made of a flexible material.

In the embodiment with the volume, e.g. a chamber, small container or sleeve having a predetermined volume, the diluted sample filled in the volume is discharged out of the discharge-opening 71' by gravitational force or by another device which pushes the diluted sample out of the chamber. For example, the chamber could be designed of a flexible material in the way of a hose or a sleeve. This hose or sleeve can then be pressed together and the filling can be discharged via the discharge-opening 71, 71'. Another preferred embodiment comprises a vent or valve 74 in the discharge device 70 that connects the volume with the outside of the tube and enables the introduction of air into the volume. This supports the flow of the diluted sample out of the discharge-opening 71, 71'. If a valve 74 is used, preferably a one-way-valve is chosen. Such a one-way-valve can also be disposed on the rotating part and be always in connection with the volume or chamber. The valve 74 restricts the leakage of the solution in the volume and is closed sealingly while the volume is filled with solution of the first container 10. However, the one-way-valve 74 allows air or a gas to enter the volume, when the solution has to be discharged from the chamber. Preferably, such a vent or valve can be activated manually.

Another aspect of the invention relates to a tube 1 for mixing, diluting, preserving and discharging a sample comprises a hollow first container 10 comprising a solution and a discharge device 70 for discharging the solution and a hollow second container 30 also comprising a solution and an introduction port 34 for introducing a sample pin 50, wherein the first container 10 and the second container 30 are connected by a transfer device 14 that enables at least a sealed transfer of the solution from the second container 30 into the first container 10. Such a tube 1 provides a safe and hygienic transfer of the solution of one container to another.

Thus, such a tube is highly practical for home use by a patient, in particular if the diluted sample has to be further processed. In particular, the first container 10 and second container 30 can be fixed together, preferably at their ends opposite to the discharge device 70 (which can be basically also a breakable discharge device of the prior art). The transfer device 14 can be a transport-pin 14 as described in this invention, but can also be for example a (preferably manually driven) sleeve pump (not shown) or hose pump (not shown) combined with one or two one-way-valves disposed at the pump device. The valve (s) enable (s) the solution to flow from the second container 30 to the first container 10, but restricts flowing in the opposite direction. Another embodiment of such a transfer device is a third tube (not shown) that is disposed between the second and the first containers and being adapted to be opened and closed to the second container 30 for being filled with the solution and for stopping the flow connection and being adapted to be opened and closed to the first container 10, to further dilute the sample of the second container 30 therein. However, a direct flow-connection between the second 30 and the first container 10 should be avoided. Thus, the third container should not be opened to the first and second containers simultaneously.

Finally, the device comprises a sample pin 50. In connection with the above mentioned tubes, any prior art sample pin with an elongated pin 51 and a handle 52, located at a proximal end of the elongated pin 51 will work properly. A very suitable prior art design comprises one or more circumferential grooves at the elongated pin.

A further design of a sample pin 50 for collecting a sample comprises an elongated pin 51 including a handle 52 located at a proximal end of the elongated pin 51 and at least one recess 54' with a predetermined volume preferably located at a distal portion of the elongated pin 51, wherein the recess 54' has the shape of a circumferential groove, that has an circumferential angle of maximum 180 degrees (this is shown in FIGS. 7*b*, 7*c*). The circumferential angle can be measured along the edge 59, with respect to the center of the elongated pin 51 and/or with respect to the inside surfaces 53 of the side edges 55' of the recess 54'. In such a sample pin 50, a more liquid sample can be better kept in the recess. The circumferential angle is measured from the center of the preferably cylindrical elongated pin 51 or from the middle of the bottom plane with respect to the top of the cutout sides of the recess 54'. Additionally, the shape of the recess is highly practical for flushing out the sample contained in the recess 54'. Furthermore, there can be two or more recesses 54' and they can be provided on opposite sides or pointing in different directions of the elongated pin 51. However, preferably two or more of these recesses 54' are facing in the same direction. In another embodiment, the bottom 56 of the recess 54' is completely flat (without the protruding middle as show in FIGS. 7*a*, 7*b*) or has a deepened shape.

An embodiment of another sample pin for collecting a sample comprises an elongated pin 51, a handle 52, located at a proximal end of the elongated pin 51 and at least one recess 54 with a predetermined volume that is preferably located at a distal portion of the elongated pin 51. This recess 54 is formed into the elongated pin, such that the elongated pin has essentially the same shape over its entire length. This recess 54 comprises only one opening with one edge, wherein the complete edge 55 of the opening is above the bottom 56 of the recess 54 when seen in a side-view and the opening is facing upwards. Thus, the recess 54 is somehow spoon-like, to avoid that a very liquid sample can escape by dripping off the sample pin 50. Preferably, there is a plurality of recesses 54 formed in the elongated pin 51. All these recesses 54 might face in the same direction.

The distal tip of the pin 51 comprises a tapered portion 57 or a rounded portion. This eases introducing the sample pin 50 into the tube 1, in particular into the transversal septum 35 of the second container 30, resp. the proximal part 30c thereof or, if the transport pin is not used, in the corresponding accommodation part including the transversal septum of the hollow first container. Furthermore the tapered or rounded portion 57 at the distal end of elongated pin 51 eases the introduction of the sample pin 50 into a very solid and/or hard sample.

The handle 52 of the sample pin 50 comprises a protrusion 58, protruding outwards from the circumference of the handle 52. This protrusion is in particular useful in connection with the guiding groove 40, 41, 42, 43 of the second container 30.

Figure 9A:
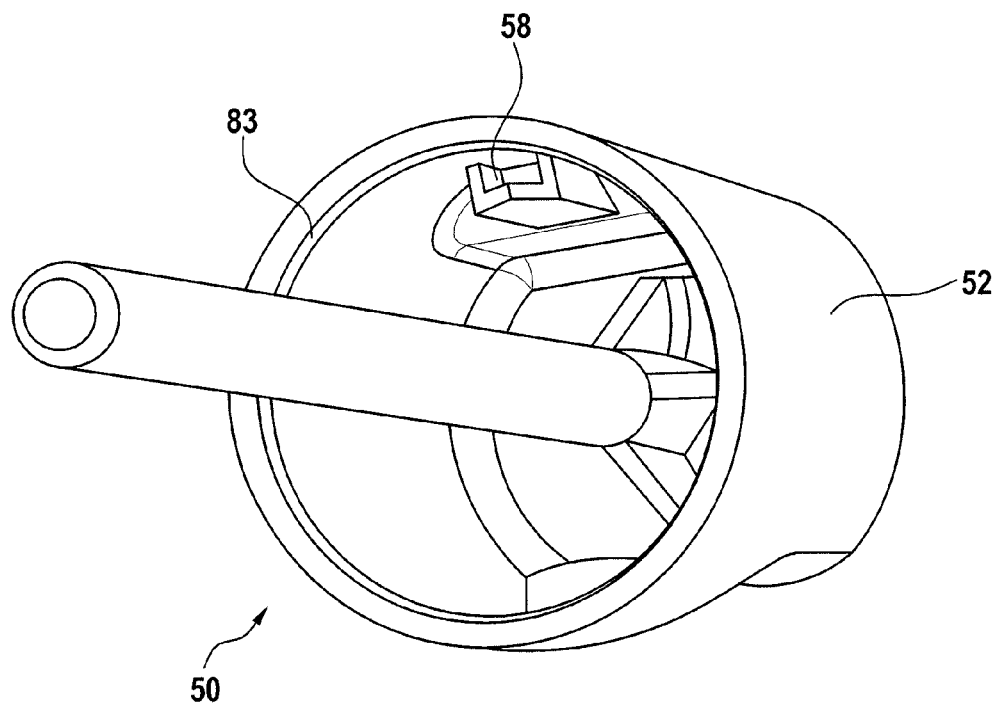
FIG. 9a, 9b show a sample pin according to an embodiment of the invention.
Figure 9B:
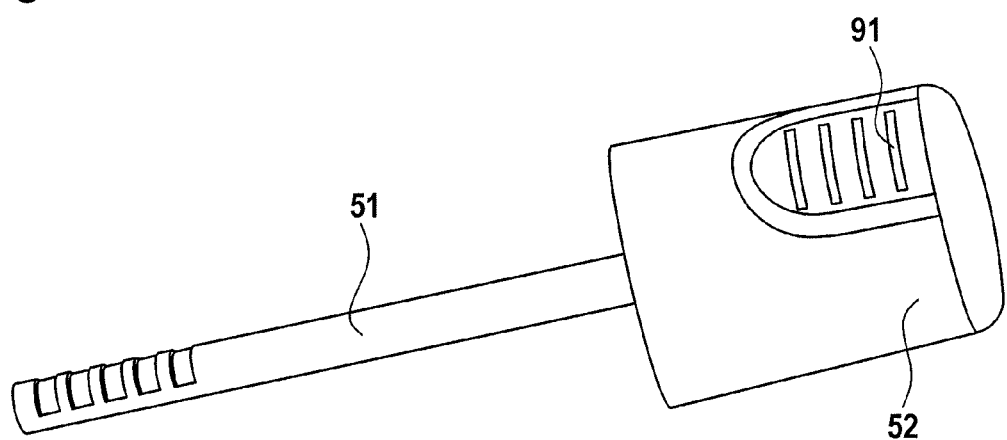

Furthermore, a sample pin can also comprise a handle 52 that has special features (see FIGS. 9*a*, 9*b*). Such a handle 52 can be used with any prior art pin or pin 51 as described above. The handle 52 comprises a locking portion 83 corresponding to the locking portions 81, 82 that can be used in the accommodation part 38 of the hollow first container 10. Preferably, there is only provided one single locking means 83 on the handle 52, but it is possible to provide more locking means, e.g. one for each locking means on the accommodation part 38. This might be the case, if the locking means have different diameters. Furthermore, the handle can comprise a gripping means 91, that serves to enable a proper manual hold of the sample pin and that can also be used as a pressing means to release the sample pin out of the first position of the first locking means.

As stated above, the sample pin can comprise a protrusion 58. In the embodiment according to FIGS. 9a and 9b, this protrusion is protruding inwards, since in this embodiment the accommodation part 38 is inserted in the inner part of the handle 52. The protruding part extends axially along the handle and can have a tapered tip on the insertion side which eases sliding the sample pin 50 along a guide 85 of the tube.

Although the locking means and the guide can each be provided alone, it is equally possible to include these features simultaneously. They can provide a synergistic effect, as explained below.

In the first position, the handle is locked in the first locking means 81. The first locking means are adjusted to hold the sample pin in the first position, but it is possible to retract the sample pin or to push it further without destroying the tube or the sample pin and by using only a relatively small force. This can be done by providing a groove and a corresponding rib which are only slightly engaging each other. Another possibility is to provide the first locking means only on a circumferential portion. The handle can then be pressed on a pressing portion 91 and is thereby deformed to release the locking means 81 of the tube from the locking means 83 of the handle, e.g. the protruding rib from the corresponding groove. Such a deformation can be very small. The first position can therefore be used as a delivery position before use of the tube. The pin 51 seals the hollow container with the solution for diluting the sample and the handle is locked in the first locking means in the first position.

The second position is for use after the sample has been collected. The sample pin is introduced back into the tube and pushed beyond the first position to the second locking means 82. These locking means are preferably very strong, so that the handle cannot be retracted once the second locking means is reached without using improper force or destroying the tube. In FIG. 10, the second locking means is therefore formed as a circumferential groove 82 (or rib) which interacts with the corresponding rib 83 (or groove) on the handle 52. Due to the circumferential shape, the pressing means cannot retract the rib out of the groove. The second position is therefore used to tightly and irreversibly close the tube. This is particularly useful to enhance the hygiene of the tube.

The guide 85 can have mainly two functions. Firstly, it is used to support opening of the handle. In the first position, the protrusion 58 is only partly (or not at all) in the receiving slot 86. By rotating the handle, the protrusion is pressed against the guide 85 and applies a force in opening direction on the handle. This is enhanced, if both of the guiding members, the guide 85 and the protrusion are formed inclined or tapered. Secondly, when the user of the sample pin is introducing the sample pin after collecting the sample, the guide 85 and the protrusion 58 are guiding the sample pin then in a predetermined position, by sliding the protrusion 58 along the guide. In the second position, the protrusion 58 is accommodated in the receiving slot 86. If so, rotation of the sample pin 50 is blocked by the side walls of the receiving slot 86 which abuts against the protrusion 58. Thus, the opening support of the guide cannot be used to open the tube once the sample pin is fixed in the second position.

A further method will now be described for use of this tube. The sample pin 50 is introduced into a sample, which can be very liquid, soft, sticky or very hard. Due to the recesses 54, it will require a little bit more pressure to force a very solid sample into the recess 54, but once in the recess 54, the sample will not fall off. Additionally, a very liquid sample is easily collected due to these recesses 54 by capillary force and/or the spoon-like structure of the recesses 54. Then, the sample pin 50 is introduced into the second container 30, thereby removing all superfluous sample adhered on the elongated pin 51 by respectively in the transversal septum 35. The protrusion 58 is guided in the guide groove 40, 41, 42, 43 and will be stopped in a first position Then the sample pin 50 is rotated into an intermediate, first locking-position (P1). The recesses 54 are now in the second container 30 and the sample in the recesses 54 can be diluted in the solution in the second container 30. This can be done by shaking the tube or by using a mixing device (e.g. a vortexer). In the preferred embodiment, the sample pin 50 is then rotated in the opposite direction following the guide groove 40, 41, 42, 43 and pressed into the accommodation part 38 of the second container 30, and will be stopped in a second locking position (P3). Thereby, the tapered end 57 of the sample pin 50 presses the transport-pin 14 into the first container 10. The transport-pin 14 comprises in the recess 15 a predetermined amount of diluted sample of the second container 30 and transports it into the first hollow container 10. This predetermined amount transferred into the hollow container 10 is then mixed with the solution contained in the first container 10. After that, the diluted sample in the first container 10 can be discharged as described above.

LIST OF REFERENCE SIGNS 1 tube
10 first container
11 through-hole
12 first end
13 second end
14 transport-pin (transfer device)
15 recess
16a latch
16b latch
17a sealing
17b sealing
18 discharge port
19 fitting element, fixing portion, protruding pin
20 extension
30 second container
30a outer tube
30b inner tube
30c proximal tube, cap
31 distal end
32 proximal end
34 opening
35 transversal septum
36 axial passageway
37 sediment portion
38 accommodating part
40 guide grooves
41 axial groove
42 circumferential groove
43 axial groove
44 wall
45 end wall
50 sample pin 51 elongated pin
52 handle
53 inside surface
54 recess
54' recess
55 edge
55' side edge
56 bottom
57 tapered portion
58 protrusion
59 edge
70 discharge device
71 discharge-opening
71' discharge-opening
73 second fitting element
74 vent/(one-way) valve
75 sealing
76 welding portion
77 moveable portion
78 volume
79 handle
81 first locking position
82 second locking position
83 locking portion on the handle
85 guide
86 receiving slot
87 guide rail
90a stopper
90b stopper
91 gripping means/pressing portion
92 abutment portion
Z (center) axis
P1 position of the protrusion
P2 position of the protrusion
P3 position of the protrusion

The invention claimed is:

1. A tube for mixing, diluting, preserving and discharging a sample, comprising:
   a hollow first container for receiving and/or storing a solution, the first container having first and second ends, closed by an end-wall, respectively, wherein the first end has a first through-hole suitable for inserting a sample pin having a shape matching to the through-hole, the second end has a discharge port suitable for discharging a diluted sample, and a first fitting element; and
   a discharge device for controlling discharge of the diluted sample via the discharge port, the device having a discharge-opening for discharging the diluted sample and a second fitting element, that is engagedly fitted with the first fitting element to mount the discharge device on the first container, wherein at least a part of the discharge device is a moveable portion that is moveable between at least a first position and a second position, wherein the first position is a closed position, in which the sample cannot be discharged, and the second position is a discharge position, in which the sample can be discharged, and the moveable portion comprises a chamber having a predetermined volume that is in the first position connected to the discharge port of the first container and in the second position connected to the discharge-opening of the discharge device.

2. The tube according to claim 1, wherein the predetermined volume is for receiving a predetermined amount of the solution.

3. The tube according to claim 2, wherein the discharge device comprises a vent or a valve connected to the volume.

4. The tube according to claim 1, wherein the discharge device further comprises a gripping device for supporting the manual actuation of the movement of the discharge device.

5. The tube according to claim 1, wherein the moveable portion is a moveable plate that serves to control the discharge of the sample.

6. The tube according to claim 5, wherein the moveable portion comprises a seal provided on at least one side of the moveable portion for sealing the discharge device from leakage of the sample.

7. The tube according to claim 1, wherein the movement of the discharge device is restricted by at least one stopper.

8. The tube according to claim 1, wherein the fitting elements are formed as protruding welding rings on the circumference of the discharge device and the second end of the hollow first container.

9. The tube according to claim 1, wherein a geometry of the discharge port and/or discharge-opening allows a quantitative and predetermined volume transfer of the liquidised and diluted sample.

10. The tube according to claim 1, wherein the second end of the hollow first container is formed detachable so as to open the first container at the second end.

11. A tube for mixing, diluting, preserving and discharging a sample, in combination with a sample pin, the tube comprises a hollow first container for receiving and/or storing a solution, wherein the hollow first container having first and second ends, wherein the first end has a first through-hole suitable for inserting a sample pin having a shape matching to the through-hole, the second end has a discharge port suitable for discharging a diluted sample, wherein the hollow first container comprises a first locking device for locking a sample pin in a first position and a second locking device for locking the sample pin in a second position, and further comprising a sample pin comprising an elongated pin, a handle located at a proximal end of the elongated pin, and at least one recess with a predetermined volume formed in a distal portion of the elongated pin, wherein the handle comprises at least one locking portion corresponding to the first and second locking devices, wherein the sample pin comprises pressing portions that serve to deform the handle to unlock the sample pin from the first locking device and wherein the second locking device prevents retraction of the sample pin.

12. The tube according to claim 11, wherein the second locking means are located further downstream than the first locking position in insertion direction.

13. The tube according to one of the claim 11, wherein the first locking means comprises a rib or a groove disposed on a circumferential portion of the first end of the hollow first container.

14. The tube according to one of the claim 11, wherein the second locking means comprises a rib or a groove disposed on a circumference of the first end of the hollow first container.

15. A tube for mixing, diluting, preserving and discharging a sample, comprising a hollow first container for receiving and/or storing a solution, the first container having first and second ends, wherein the first end has a first through-hole suitable for inserting a sample pin having a shape matching to the through-hole, the second end has a discharge port suitable for discharging a diluted sample, wherein the hollow first container has a guide disposed on the first end of the first hollow container which interacts with the sample pin to guide the sample pin in a predetermined position, further comprising a sample pin, wherein the hollow first container further comprises first locking means for locking a sample pin in a first position and second locking means for locking the sample pin in a second position.

\* \* \* \* \*